United States Patent [19]
Zoeller et al.

[11] Patent Number: 5,936,117
[45] Date of Patent: Aug. 10, 1999

[54] CARBONYLATION OF OLEFINS

[75] Inventors: Joseph Robert Zoeller; Elizabeth MacGowan West, both of Kingsport; Horace Lawrence Browning, Jr., Fall Branch; George Geiger Mayfield, Kingsport, all of Tenn.

[73] Assignee: Eastman Chemical Company, Kingsport, Tenn.

[21] Appl. No.: 08/509,039

[22] Filed: Jul. 28, 1995

Related U.S. Application Data

[63] Continuation-in-part of application No. 08/351,920, Dec. 8, 1994, abandoned.

[51] Int. Cl.[6] ..................................................... C07C 67/38
[52] U.S. Cl. ........................... 560/233; 562/521; 562/890
[58] Field of Search ............................... 560/247; 11/233; 502/305; 562/521, 890

[56] References Cited

U.S. PATENT DOCUMENTS 4,323,698  4/1982  Haag .

FOREIGN PATENT DOCUMENTS 1159474  12/1983  Canada .
721409    3/1980   U.S.S.R. .

*Primary Examiner*—Michael L. Shippen
*Attorney, Agent, or Firm*—Michael J. Blake; J. Frederick Thomsen; Harry J. Gwinnell

[57] ABSTRACT

Disclosed is a process for the preparation of aliphatic carbonyl compounds selected from aliphatic carboxylic acids, alkyl esters of aliphatic carboxylic acids and anhydrides of aliphatic carboxylic acids by the carbonylation of olefins in the presence of a catalyst system comprising (1) a primary component selected from at least one Group 6 metal, i.e., chromium, molybdenum, and/or tungsten and (2) a secondary component selected from at least one of certain halides and tertiary and quaternary compounds of a Group 15 element, i.e., nitrogen, phosphorus and/or arsenic. The process constitutes and improvement over known processes since it can be carried out at moderate carbonylation conditions without the necessity of using an expensive noble metal catalyst, volatile, toxic materials such as nickel tetracarbonyl, formic acid or a formate ester.

6 Claims, No Drawings

CARBONYLATION OF OLEFINS

This application is a continuation-in-part of our copending appplication Ser. No. 08/351,920 filed Dec. 08, 1994, now abandoned.

This invention pertains to a process for the preparation of oxygenated compounds by the carbonylation of olefins. More specifically, this invention pertains to the preparation of oxygenated compounds such as carboxylic acids, esters and anhydrides by contacting carbon monoxide with a mixture of an olefin and a catalyst system comprising a Group 6 metal and a halide selected from the compounds of chlorine, bromine and iodine.

Carboxylic acids and their anhydrides and esters have a variety of uses in the chemical industry. For example, propionic acid and certain of its salts are used as preservatives in the animal feed and food industries. The anhydrides of propionic and butyric acids are used in the manufacture of cellulose esters which find a number of uses in the plastics industry.

Acetyl compounds such as acetic acid, acetic anhydride and methyl acetate are manufactured by very efficient process by the carbonylation of methanol and/or methyl acetate in the presence or absence of water, depending on the desired product. Aliphatic, carboxylic acids containing 8 or more carbon atoms are readily available from natural occurring substances such as natural occurring fats and oils. A need exists for efficient processes for the direct manufacture of aliphatic, carboxylic acids containing 3–9 carbons. At the present time, the major volume of these $C_3$–$C_9$ carboxylic acids are manufactured on a commercial scale by one of 2 methods. This first consists of the sequential hydroformylation and oxidation of olefins as illustrated by equations (1) and (2):

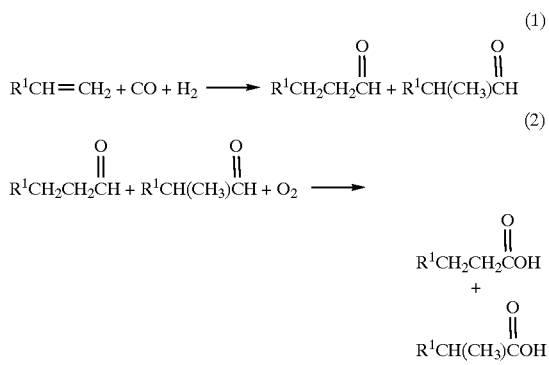

The second commercial process involves the oxidation of butane or unsaturated natural acids. Any derivatives of the carboxylic acids require an additional chemical processing step. For example, propionate esters can be made by esterification of propionic acid with alcohols, using a variety of catalysts known in the art, and propionic anhydride can be prepared from propionic acid by an exchange reaction with acetic anhydride.

Hydroxycarbonylation (also referred to as hydrocarboxylation), depicted in equation (3), represents a direct (one step) process for the preparation of carboxylic acids. More importantly, it offers an advantage in the direct production of derivatives such as esters and anhydrides of the lower carboxylic acids. As exemplified in equations (4) and (5), these processes have the potential to directly generate the carboxylic acid derivative in a single step using an olefin and carbon monoxide, thus eliminating multiple processing steps.

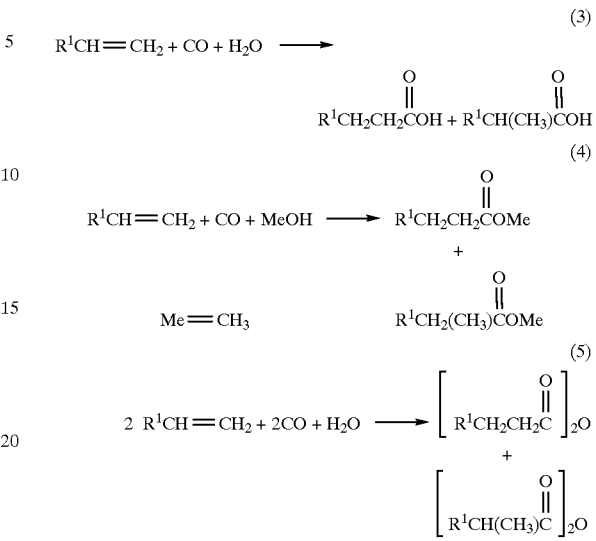

The chemistry involved in equations (3), (4) and (5) is well known as evidenced by Pino, et al., Organic Syntheses via Metal Carbonyls, Eds. I. Wender and P. Pino, Vol. 2, John Wiley & Sons, Inc., New York, N.Y., pages 233–296 (1977); Mullen, New Syntheses With Carbon Monoxide, Ed. J. Falbe, Springer-Verlag, Berlin, Germany, pages 275–286 (1980); Colquhoun, et al., Carbonylation—Direct Synthesis of Carbonyl Compounds, Plenum Press New York, N.Y., pages 102–106, 119–130 (1991); and Forster, et al., Catalysis Rev.—Sci. Eng., 23, 89 (1981). However, this chemistry apparently has been used commercially in only a single high pressure, high temperature hydroxycarbonylation unit for the manufacture of propionic acid as the sole product. See Samel, et al., "Propionic Acid and Derivatives", in Ullman's Encyclopedia of Industrial Chemistry, 5th edit., Vol. A22, VCH Publishers, New York, N.Y., page 223 (1993). This propionic acid process uses a highly toxic (and very volatile) $Ni(CO)_4$ catalyst and high pressures (>186 bar, 2700 psi) which requires specialized high pressure equipment. Furthermore, the high temperatures (>270° C.) lead to excessive corrosion and, therefore, require the use of an expensive silver lined reactor. The operating conditions are more clearly defined in Bertleff, "Carbonylation", in Ullman's Encyclopedia of Industrial Chemistry, 5th edit., Vol. A5, VCH Publishers, New York, N.Y., page 223 (1986).

Processes utilizing moderate pressures and temperatures in the chemistry of equations (3), (4) and (5) are described in the Pino, et al., Mullen, Colquhoun, et al., and Forster, et al. references cited above, in U.S. Pat. Nos. 3,579,551, 3,579,552, 3,816,488, 3,816,489, 3,818,060, 3,821,265 and 3,852,346, and in Bittler, et al., Ang. Chem., Int. Ed. 7, 329 (1968) and Tsuji, Organic Synthesis With Palladium Compounds, Springer-Verlag, Berlin, Germany, pages 81–84 (1980). These processes require an expensive catalyst such as a rhodium, iridium, or palladium catalyst and none have been used on a commercial basis. The propensity of rhodium, iridium, or palladium based catalyst to precipitate, especially during product separation, is well known and has led to the development of technology directed to the stabilization of these catalysts during product separation. Moderate pressure processes utilizing a cobalt-iodide or nickel-iodide catalyst systems are described in U.S. Pat. Nos. 3,944,604, 3,989,751, 3,946,055 and 3,980,683.

The carbonylation of olefins in the presence of rhodium-iodide-Group VIA metal and iridium-iodide-Group VIA metal catalyst systems are described in U.S. Pat. No. 3,821,265. Chromium or molybdenum is included in this process to stabilize the rhodium or iridium catalyst complex during distillation.

The preparation of carboxylic acids, esters and anhydrides by the carbonylation of olefins in the presence of a catalyst system comprising (1) a nickel compound, (2) a Group 6 metal, i.e., chromium, molybdenum, or tungsten, (3) a trivalent phosphine, a trivalent amine or an alkali metal, and (4) a halide, e.g., an iodine compound, is described in U.S. Pat. Nos. 4,372,889, 4,407,726, 4,625,055, 4,537,871, 4,335,058, 4,483,803, 4,354,036, 4,540,811. The toxicity of $Ni(CO)_4$, which is likely generated in the system, still represents a problem and a disadvantage.

The inventors of the present invention are unaware of any patents or other publications describing the carbonylation of olefins with a Group 6 metal as the sole metal component. However, Group 6 metals have been used to induce carbonylations with other substrates and to induce the formation of esters and acids via the addition of formate derivatives to olefins. For example, Imbeaux, et al., J. Chem. Soc., Chem. Comm., 1678–1679 (1992) disclose the use of fluoride ions to induce the conversion of alkyl iodides and diiodides to esters and lactones, respectively, using stoichiometric amounts of $Mo(CO)_6$. U.S. Pat. No. 3,790,607 describes a high pressure process for carbonylation of fluorocarbon iodides to esters using a series of metal carbonyls including carbonyl compounds of the Group 6 metals. The substrates in both cases are iodides, not olefins, and are used either stoichiometrically or demonstrate limited catalysis.

U.S. Pat. No. 4,558,153 describes the addition of formates to olefins using a catalyst comprising a Group 6 metal, a halide, and optionally, a phosphorus-containing promoter. The source of the carbonyl unit in the process of desribed in this patent is formic acid or a formate ester which must be formed in a separate manufacturing operation. At no point does U.S. Pat. No. 4,558,153 contemplate the addition of carbon monoxide to an olefin to generate the carbonyl unit. In fact, no carbon monoxide is used in most of the examples of the patent.

Finally, the use of Group 6 metal oxides, especially tungsten oxide, formulated as $W_2O_5$, as heterogeneous catalysts for the carbonylation of alcohols is disclosed in U.S. Pat. Nos. 1,998,218, 1,998,219 and 1,998,220. However, the function of the Group 6 metal oxides is to act as strong acids and the reactions were carried out at very high pressures and temperatures, i.e., about 193 bar (2800 psi) and 375° C.

The present invention provides a process for the preparation of an aliphatic carbonyl compound selected from aliphatic carboxylic acids, alkyl and aryl esters of aliphatic carboxylic acids, and anhydrides of aliphatic carboxylic acids. The process comprises contacting carbon monoxide with a mixture comprising an olefin and a catalyst system comprising (1) a primary component selected from at least one Group 6 metal, i.e., chromium, molybdenum, tungsten, or a mixture thereof and (2) a secondary component selected from at least one of:

(i) a halide selected from the compounds of chlorine, bromine or iodine;

(ii) an alkali metal compound;

(iii) a salt of a quaternary organic compound of a Group 15 element;

(iv) a trisubstituted organic compound of a Group 15 element; and (v) an oxide of a trisubstituted phosphine compound;

under carbonylation conditions of temperature and pressure, wherein the process is carried out in the substantial absence of (1) metals of Groups 8, 9 and 10, i.e., Fe, Ru, Os, Co, Rh, Ir, Ni, Pd and Pt and (2) formic acid and formate esters. The advantages and benefits provided by the invention include (1) the elimination of expensive noble metals such as rhodium and iridium; (2) the essential absence of nickel removes the potential problem of $Ni(CO)_4$ hazards while coincidentally leading to higher rates; and (3) the expectation that product separation and catalyst recycle will pose fewer problems. Another benefit of the present invention is that neither formic acid nor a formate ester is required in the operation of the process. The requirement that the process is carried out in the substantial absence of formic acid or a formate ester means that all, or substantially all, e.g., at least 95 mole percent, of the carbonyl units of the carbonyl compounds obtained from the process is obtained from carbon monoxide rather than formic acid.

The primary and essential component of the catalyst system provided by the invention can be any of the Group 6 elements (IUPAC classification), i.e., chromium, molybdenum, tungsten, or a mixture thereof. However, molybdenum is the most active element and, therefore, is preferred. The Group 6 metal can, in principle, be added as any of a variety of Group 6 metal-containing compounds. However, the most active metal, molybdenum, is generally available in its various oxide forms or as its hexacarbonyl derivative, with the later being preferred.

The catalytically-effective amount of the Group 6 metal can be varied widely but the concentration of the metal in the liquid reaction medium typically will be in the range of about 0.0001 to 1 molar with a concentration of about 0.005 to 0.5 molar being preferred. For the preferred molybdenum system, these molar ranges correspond to weight concentrations in the range of 10 to 96,000 ppm and 50 to 48,000 ppm Mo.

The chloride, bromide, or iodide component can be added in any number of forms such as, for example, an alkyl halide, a hydrogen halide, a salt such as a halide salt of catalyst components (2)(ii) and (2)(iii) defined above, elemental halide, or any combination thereof. The halide component preferably is an iodide. When a halide component is present, the atomic ratio of Group 6 metal:$X^-$ (wherein X is Cl, Br or I) is about 1:1 to about 1:1000, preferably about 1:1 to 1:100.

Examples of the alkali metal compounds of component (2)(ii) include the halides, especially the iodides, and the alkyl carboxylates of lithium, potassium, rubidium, and/or cesium. Examples of the salts of quaternary organic compounds of a Group 15 (IUPAC classification) element, i.e. nitrogen, phosphorus and arsenic, and the trisubstituted organic compound of a Group 15 element include compounds have the general formulas"

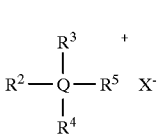
(I)

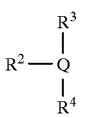
(II)

wherein $R^2$, $R^3$, $R^4$ and $R^5$ are hydrocarbyl groups containing up to about 20 carbon atoms, Q is N, P or As and X is an anion. Because of their availability, the compounds containing nitrogen or phosphorus generally are preferred. Examples of the hydrocarbyl groups are alkyl of up to 20 carbon atoms including aryl substituted alkyl such as benzyl, cycloalkyl of 5 to 7 ring carbon atoms; and aryl such as phenyl and substituted phenyl such as tolyl. Examples of anion X include halogen. The quaternary organic compounds of a Group 15 element and the trisubstituted organic compound of a Group 15 element also may be a heterocyclic nitrogen-containing compound such as pyridine, quinoline, imidazole, N-methylpyridinium halide, N,N'-dimethylimidazolium halide, and the like; or a bisphosphine compound such as 1,2-bis(diphenylphosphino)ethane.

Examples of the trisubstituted phosphine oxides include compounds having the formula

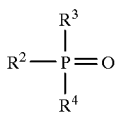

(III)

wherein $R^2$, $R^3$, and $R^4$ are defined above. Based on its low volatility and ready availability, trioctylphosphine oxide is particularly preferred. NMR analyses indicates that the use of trisubstituted phosphines of formula (II) in the most active systems results in the in situ conversion of the phosphine to a quaternary phosphonium or phosphine oxide compound.

Components (2)(i), (2)(ii), (2)(iii), (2)(iv) and (2)(v) may be used individually or in combination. The total amount of components (2)(ii), (2)(iii), (2)(iv) and (2)(v) which may be used range from 1 to 200, preferably 1 to 30 gram atoms [in the case of component (2)(ii)] or moles [in the case of components (2)(iii), (2)(iv) and (2)(v)] per gram atom of Group VIA metal. The optimal combination of secondary catalyst components depends to a great extent on the nature of the olefin reactant, the product being produced, and the resultant design considerations. However, the preferred catalyst systems comprises (A) a Group 6 metal, especially molybdenum, (B) at least 1 iodine compound and (C) at least 1 component selected from an alkali metal salt, a salt of a quaternary phosphonium compound, a trisubstituted phosphine or a trisubstituted phosphine oxide. The iodine compound(s) (B) may be provided as the iodide salt of any of the compounds constituting component (C). However, iodine compound (B) more typically is provided as hydrogen iodide and/or an alkyl iodide, e.g., an alkyl iodide containing up to about 8 carbon atoms. When an alkyl iodide is used in the process, it preferably will correspond to the olefin reactant, e.g., ethyl iodide when the olefin reactant is ethylene. Thus, in the carbonylation of ethylene to produce propionic acid and/or propionic anhydride, a catalyst system consisting essentially of molybdenum as molybdenum hexacarbonyl, iodine as ethyl iodide, lithium as lithium iodide and trioctylphosphine oxide has been found to possess good to excellent activity and stability.

The minimum operable pressure is dependent upon a plurality of factors such as the nature of the olefin being used since the olefin exerts a vapor pressure dependent upon chain length, temperature, the particular catalyst system employed and the concentration of the various catalyst components. Generally, the process may be operated over a range of about 8 to 346 bar absolute (approximately 116 to 5020 pounds per square inch absolute—psia) total pressure with the preferred pressure range being about 18 to 104 bar absolute (approximately 261 to 1509 psia). For ethylene carbonylation, a total pressure in the range of about 28.6 to 83 bar is particularly preferred.

The present carbonylation process generally may be carried out at temperatures in the range of about 75 to 350° C., preferably 150 to 250° C., and most preferably 150 to 200° C. The carbon monoxide may be employed in substantially pure form, as available commercially, but inert diluents such as carbon dioxide, nitrogen, methane, and noble gases can be present if desired. The presence of inert diluents does not affect the carbonylation reaction but their presence makes it necessary to increase the total pressure in order to maintain the desired CO partial pressure. The presence of minor amounts of water such as may be found in the commercial forms of the reactants is, however, entirely acceptable. The gas fed to the carbonylation process preferably comprises carbon monoxide containing up to about 50 volume percent hydrogen. The presence of hydrogen has been found to have a favorable effect on the rate of carbonylation.

Although the olefin can be selected from a long list of ethylenically-unsaturated compounds, e.g. olefins containing from 2 to 20 carbon atoms, there is a limitation inherent in the choice of olefin. For example, the hydroxycarbonylation of higher olefins with the catalyst system described herein introduces a carboxyl or carboxylate group at any one of the carbons along the carbon chain. For example, hydroxycarbonylation of 1-pentene gives mixtures of hexanoic acid, 2-methylvaleric acid, and 2-ethylbutyric acid. A means for controlling the distribution of products for olefins having 5 or more carbons has not yet been discovered. Therefore, the utility of the present carbonylation process for the generation of higher acids ($C_6$ or higher) is limited to systems in which the mixture is either tolerated or preferred. Internal olefins are also useful in this reaction, but again lead to mixtures of products. Thus, the preferred olefin reactants consist of $C_2$–$C_4$ α-olefins, i.e., ethylene, propylene, and the butenes, where there are, at most, only two potential products which are readily separable.

The process may be operated in a batch, semi-continuous or continuous mode. Hydroxycarbonylation rates can be enhanced dramatically by using production systems designed for very efficient mass transfer, especially when light ($C_2$ to $C_4$) olefins are employed.

The process is carried out in the presence of an organic solvent or diluent such as, for example, carboxylic acids and esters, hydrocarbons, e.g., octane, benzene, toluene, xylene and tetralin, or halogenated hydrocarbons such as the chlorobenzenes, e.g., trichlorobenzene, or carboxylic acids, or esters such as cellosolve acetate, and the like. In certain instances a material may serve as both solvent and reactant. For example, aliphatic carboxylic acid anhydrides may be prepared by the carbonylation of an olefin in the presence of a carboxylic acid under substantially anhydrous conditions. In this embodiment of the process, the carboxylic acid functions as both a process solvent and as a reactant. Mixtures of solvents can also be used, such as mixtures of ethyl propionate and propionic acid. The carboxylic acid, when used, should preferably correspond to the acid, or the acid moiety of the anhydride, being produced since the preferred solvent is one that is indigenous to the system, e.g., propionic acid and/or ethyl propionate in the case of ethylene carbonylation. When not a reactant or the product itself, the solvent or diluent preferably has a boiling point sufficiently different from the desired product in the reaction mixture so that it can be readily separated, as will be apparent to persons skilled in the art.

The reaction should be run in the presence of a minimum amount of corrosion metals. As demonstrated in the accompanying examples, we have found that typical corrosion metals, particularly nickel and iron, inhibit carbonylation rate and, therefore, as is specified hereinabove, the carbonylation process is operated in the substantial absence, e.g., less than 300 parts per million (ppm), of the metals of Groups 8, 9 and 10, in general, and nickel and iron, in particular. The inhibition caused by nickel differentiates the present carbonylation process of this invention from the processes described in U.S. Pat. Nos. 4,372,889, 4,407,726, 4,625,055, 4,537,871, 4,335,058, 4,483,803, 4,354,036, 4,540,811 wherein nickel is the primary component of the catalyst systems disclosed therein.

The primary utility of processes provided by the present invention is the preparation of carboxylic acids containing 3 to 9 carbon atoms, preferably carboxylic acids containing 3 to 5 carbon atoms, and most preferably propionic acid, and the anhydride of such carboxylic acids by the carbonylation of the appropriate olefin. In the manufacture of carboxylic acids, water is included in the carbonylation mixture comprising an olefin, an inert, organic solvent and a catalyst system according to the preceding description. Typically, the amount of water fed to the carbonylation zone is at least 1 mole per mole of olefin and preferably is from 1 to 3 moles of water per mole of olefin. The manufacture of carboxylic anhydrides is carried out under substantially anhydrous condition as is well known in the art. A mixture of carboxylic acids and anhydrides can be produced by carrying out the process in the presence of a limited amount of water.

The carbonylation process of the present invention is further illustrated by the following examples. For the pentene carbonylation experiments, analyses were performed by gas chromatography (GC) using a Hewlett Packard 5890 GC using a 75M (0.53 mm inside diameter, 2.5 micron film) Quadrex 007 CMPS Capillary Column and nonane as an internal standard. A split injection was used to introduce the sample and sample detection was accomplished with TCD detector. For the ethylene carbonylation experiments, analyses were performed by GC using a Hewlett Packard 5890 GC using a 25M (0.25 mm inside diameter, 0.25 micron film) Quadrex 007 FFAP Capillary Column and p-xylene as an internal standard. A split injection was used to introduce the sample and sample detection was accomplished with TCD detector. The pressures given are total pressures in bars absolute.

EXAMPLE 1

A solution of 5.1 g of 47% aqueous hydrogen iodide (0.0187 moles of HI), 8 grams of water, was diluted to 115 g with propionic acid as solvent. The total amount of water present, including the HI solution, was 0.6 moles. This solution was added to a 300 mL, mechanically-stirred, corrosion-resistant autoclave containing 1.45 g (0.0055 moles, 5.5 mmol) of molybdenum hexacarbonyl ($Mo(CO)_6$) and 6.55 g (0.025 mol, 25 mmol) of triphenylphosphine ($Ph_3P$). The autoclave then was sealed and thoroughly flushed with nitrogen.

1-Pentene (35 g, 0.5 moles) then was added to the autoclave via a high-pressure, liquid addition funnel. The system then was pressurized to 2.7 bar (39 psia) with hydrogen and then to 7.9 bar (115 psia) with carbon monoxide. The mixture was heated to 175° C., which typically brought the pressure to 21.7 to 25.1 bar (315–350 psi) and then the pressure was adjusted to 35.5 bar (515 psi) with carbon monoxide. The reaction was maintained at 175° C. and 35.5 bar for 5 hours, adding carbon monoxide as needed to maintain the pressure. The autoclave then was cooled, vented, and a sample removed and analyzed for 1-pentene, trans-2-pentene, cis-2-pentene, hexanoic acid, 2-methylvaleric acid and 2-ethylbutyric acid. The 2-methylvaleric acid and 2-ethylbutyric acid were not completely separable and are reported together as branched $C_6$ acids. The results of the analysis are shown in Table I. The value reported in Table I for each component is the weight percent of the component present in the reaction mixture.

EXAMPLE 2

A solution of 10.7 grams of water (0.6 moles) in 104.3 g of propionic acid was added to a 300 mL mechanically-stirred, corrosion-resistant autoclave containing 2.90 g (0.011 moles, 11 mmol) of molybdenum hexacarbonyl ($Mo(CO)_6$) and 1.02 g (0.01 moles) of lithium acetate dihydrate ($LiOAc.2H_2O$). The autoclave then was sealed and thoroughly flushed with nitrogen.

1-Pentene (35 g, 0.5 moles) then was added to the autoclave via a high-pressure, liquid addition funnel. The system then was pressurized to 2.7 bar (29 psia) with hydrogen and then to 7.9 bar (115 psia) with carbon monoxide. The mixture was heated to 200° C. and then the pressure was adjusted to 35.5 bar (515 psia) with carbon monoxide. The reaction was maintained at 200° C. and 35.5 bar for 5 hours, adding carbon monoxide as needed to maintain the pressure. The autoclave then was cooled, vented, and a sample was removed and analyzed for 1-pentene, trans-2-pentene, cis-2-pentene, hexanoic acid, 2-methylvaleric acid and 2-ethylbutyric acid. As in Example 1, 2-methylvaleric acid and 2-ethylbutyric acid are reported together as branched $C_6$ acids. The results of the analysis are shown in Table I. This example demonstrates that, with proper choice of catalyst copromoter, the halide may be optional but results in a process that is inferior even when employing more catalyst and higher temperatures.

EXAMPLE 3

The procedure described in Example 1 was repeated except the triphenylphosphine was omitted. The analytical data obtained are shown in Table I. This example shows that the Group 6 metal and an iodine component are sufficient for catalysis, but inferior to systems containing additional copromoters.

Comparative Example 1

Example 1 was repeated except the that $Mo(CO)_6$ was omitted. From the analytical data shown in Table 1, only a very minor quantity of isomeric $C_6$ carboxylic acids can be detected. This example shows that the Group 6 metal is necessary.

EXAMPLE 4

The procedure described in Example 1 was repeated except that 6.95 g (25 mmol) triphenylphosphine oxide ($Ph_3PO$) was used in place of triphenylphosphine. The analytical data obtained are shown in Table I. This example demonstrates the utility of oxides of Group 15.

EXAMPLE 5

The procedure described in Example 1 was repeated except that 1.94 g (0.0055 mol) tungsten hexacarbonyl ($W(Co)_6$) was used in place of $Mo(CO)_6$. The analytical data obtained are shown in Table I.

EXAMPLE 6

A solution of 10.2 g of 47% aqueous hydrogen iodide (0.0394 moles of HI), 6.93 grams of water, was diluted to 115 g with propionic acid as solvent. The total water present, including the HI solution, was 0.6 moles. This solution was added to a 300 mL, corrosion resistant, mechanically stirred autoclave containing 3.87 g (0.011 moles, 11 mmol) of tungsten hexacarbonyl (W(Co)$_6$) and 13.9 g (0.05 mol) of triphenylphosphine oxide. The autoclave then was sealed and thoroughly flushed with nitrogen.

1-Pentene (35 g, 0.5 moles) was added to the autoclave via a high-pressure, liquid addition funnel. The system then was pressurized to 2.7 bar (29 psia) with hydrogen and then to 7.9 bar (115 psia) with carbon monoxide. The mixture was heated to 200° C. and then the pressure was adjusted to 52.7 bar (765 psia) with carbon monoxide. The autoclave was maintained at 200° C. and 52.7 bar for 5 hours, adding carbon monoxide as needed to maintain the pressure. The autoclave then was cooled, vented, and a sample was removed and analyzed for 1-pentene, trans-2-pentene, cis-2-pentene, hexanoic acid, 2-methylvaleric acid and 2-ethylbutyric acid. As in Example 1, 2-methylvaleric acid and 2-ethylbutyric acid are reported together as branched C$_6$ acids. The results of the analysis are shown in Table I.

EXAMPLE 7

The procedure described in Example 1 was repeated except that 1.21 g (0.0055 mol) chromium hexacarbonyl (Cr(CO)$_6$) was used in place of Mo(CO)$_6$. The results of the analysis are shown in Table I. This example demonstrates the use of chromium as the Group VIA metal component of the catalyst system.

EXAMPLE 8

The procedure of Example 6 was repeated except 2.42 g (0.011 mol) chromium hexacarbonyl (Cr(CO)$_6$) was used in place of W(CO)$_6$ and the HI was replaced with 2.50 g (0.037 mol) of LiI. The results of the analysis are shown in Table I. This example serves to demonstrate both the use of chromium as the primary catalyst component and the use of an alternative iodide source (LiI).

EXAMPLE 9

The procedure described in Example 1 was repeated except that 19 mmol of HCl (added as concentrated hydrochloric acid) was used in place of HI. The results of the analysis are shown in Table I and indicate that, although inferior to iodide, chloride is useful as the halide component of the catalyst.

EXAMPLE 10

The procedure of Example 9 was repeated except that 6.95 g (0.025 mol) of Ph$_3$PO was added in addition to the Ph$_3$P already present. The analytical results are shown in Table 1 and further demonstrate that chloride is an operable, albeit inferior, halide component.

EXAMPLE 11

The procedure of Example 4 was repeated except that hydrogen bromide (HBr, 19 mmol as a concentrated, aqueous HBr solution) was used in place of HI. The analytical data obtained from this example are shown in Table 1 and indicate that bromide is a useful but inferior halide component of the catalyst system.

EXAMPLE 12

The procedure of Example 4 was repeated except that 2.50 g (19 mmol) of LiI was used in place of the HI component. The analytical data obtained from this example are shown in Table 1 and establish the use of LiI as both the source of halide component and the copromoter.

EXAMPLE 13

The procedure described in Example 1 was repeated except that the aqueous hydrogen iodide was replaced with 2.37 g (9.4 mmol as I$_2$) of molecular iodine 1.43 g water. The results of the analysis are shown in Table I and demonstrate the use of a different iodine source.

EXAMPLE 14

The procedure described in Example 1 was repeated except that the amount of aqueous hydrogen iodide was lowered to 1.5 g of 47% aqueous HI (0.0055 mol of HI). The results of the analysis are shown in Table I. This procedure and catalyst system gave higher amounts of the normal isomer (n-hexanoic acid).

EXAMPLE 15

The procedure of Example 1 was repeated except that a pressure of 52.7 bar (765 psia) was used over the 5 hour reaction period. The results of the analysis are shown in Table I.

EXAMPLE 16

The procedure described in Example 1 was repeated except that a pressure of 69.9 bar (1015 psia) was used over the 5 hour reaction period. The results of the analysis are shown in Table I.

EXAMPLE 17

The procedure described in Example 12 was repeated except that the reaction was run at 52.7 bar (765 psi) and 200° C. The analytical results obtained from this experiment are shown in Table 1. The use of higher temperature and pressure raised the total amount of carboxylic acids formed.

EXAMPLE 18

A solution of 10.2 g of 47% aqueous hydrogen iodide (0.0394 moles of HI), 6.93 grams of water, was diluted to 150 g with propionic acid as solvent. The total water present, including aqueous HI solution, was 0.6 moles. This solution was added to a 300 mL, mechanically-stirred, corrosion-resistant autoclave containing 2.90 g (0.011 moles, 11 mmol) of molybdenum hexacarbonyl (Mo(CO)$_6$) and 19.3 g (0.05 mol) of trioctylphosphine oxide. The autoclave then was sealed and thoroughly flushed with nitrogen.

1-Pentene (35 g, 0.5 moles) was added to the autoclave via a high-pressure, liquid addition funnel. The system then was pressurized to 2.7 bar (29 psia) with hydrogen and then to 7.9 bar (115 psia) with carbon monoxide. The mixture was heated to 200° C. and then the pressure was adjusted to 52.7 bar (765 psia) with carbon monoxide. The reaction was maintained at 200° C. and 52.7 bar for 5 hours, adding carbon monoxide as needed to maintain the pressure. The autoclave then was cooled, vented, and a sample removed and analyzed for 1-pentene, trans-2-pentene, cis-2-pentene, hexanoic acid, 2-methylvaleric acid and 2-ethylbutyric acid. As in Example 1, 2-methylvaleric acid and 2-ethylbutyric acid are reported together as branched C$_6$ acids. The results of the analysis are shown in Table I.

EXAMPLE 19

The procedure described in Example 8 was repeated using 19.3 g (0.05 mol) of trioctylphosphine oxide in place of the triphenylphosphine oxide. The analytical data obtained from this example are shown Table I.

EXAMPLE 20

The procedure of Example 6 was repeated except that 35 g (0.5 moles) of 2-pentene were used in place of 1-pentene and the W(Co)$_6$ was replaced with 2.90 g (0.011 moles) of Mo(CO)$_6$. The analytical results obtained are shown in Table I. This example demonstrates that internal olefins are useful in this process as well. It also serves to demonstrate that the isomerization of the olefins observed in this process is not important since the isomers also lead to the generation of the desired carboxylic acids.

TABLE I

| Example | 1-Pentene | 2-Pentenes | Branched C6 Acids | Hexanoic Acid |
|---|---|---|---|---|
| 1 | 0.6 | 2.3 | 15.3 | 7.7 |
| 2 | 10.9 | 4.1 | 2.2 | 0.9 |
| 3 | 1.5 | 8.6 | 1.1 | 3.0 |
| C-1 | 4.8 | 8.2 | 0.3 | trace |
| 4 | 2.9 | 11.5 | 7.2 | 4.0 |
| 5 | 0.7 | 6.6 | 4.9 | 5.5 |
| 6 | 0.5 | 4.5 | 8.4 | 1.6 |
| 7 | 1.5 | 7.1 | 3.9 | 4.5 |
| 8 | 0.7 | 7.5 | 2.1 | 3.2 |
| 9 | 2.8 | 2.6 | 0.6 | 1.6 |
| 10 | 5.2 | 4.0 | 0.7 | 2.2 |
| 11 | 3.3 | 7.2 | 0.3 | 2.2 |
| 12 | 0.9 | 11.7 | 2.2 | 3.9 |
| 13 | 0.6 | 7.4 | 5.4 | 5.4 |
| 14 | 0.5 | 7.5 | 6.4 | 10.8 |
| 15 | 0.3 | 6.4 | 6.6 | 6.8 |
| 16 | 0.9 | 5.7 | 7.2 | 7.3 |
| 17 | 0.9 | 8.0 | 7.4 | 2.6 |
| 18 | 0.8 | 9.5 | 6.5 | 2.4 |
| 19 | 0.5 | 6.9 | 2.0 | 2.8 |
| 20 | 0.8 | 15.7 | 4.1 | 3.3 |

EXAMPLE 21

A solution consisting of 72 g (4.0 moles) water, 54.6 g ethyl iodide (EtI), and 178 g (2.97 moles) of acetic acid was added to a 1 L, mechanically-stirred, corrosion-resistant autoclave containing 5.81 g (0.022 moles) of Mo(CO)$_6$ and 38.6 g (0.1 moles) of tetrabutylphosphonium iodide (Bu$_4$PI). (The acetic acid acts as both solvent and internal standard for the reaction.) The autoclave, which was equipped with a dip tube for sampling, was sealed, tested for leaks with nitrogen, and then pressurized successively with 6.9 bar (100 psi) increments of hydrogen, carbon monoxide, and finally with ethylene.

The autoclave was then heated to 180° C. and then the pressure was adjusted to 55.1 bar (800 psi) using a mixture of 1:1 ethylene:carbon monoxide. These conditions were maintained for 90 minutes. The progress of the reaction was monitored by removing and analyzing liquid samples via the dip tube every 8 minutes for the first hour of the reaction. After the 90 minute reaction period had elapsed, the reaction was cooled and vented. The resultant solution was analyzed for ethyl acetate, ethyl propionates, acetic acid, and propionic acid.

The moles of propionyl groups generated (the sum of the propionic acid and ethyl propionate) can be determined from the GC data using the following formula:

$$n_p = \frac{[(X_{pa}/74) + (X_{ep}/102)]}{[(x_{ea}/88) + (X_{aa}/60)]} \cdot n_{ao}$$

wherein
n=moles
X=weight fraction (obtained from GC analysis)
n$_p$=total moles of propionyl products
n$_a$°=moles of acetyl initially present=acetic acid added at start and wherein ep=ethyl propionate; pa=propionic acid; ea=ethyl acetate; and aa=acetic acid.

The results of the analysis are shown in Table II. The value reported in Table II for each component is the weight percent of the component present in the reaction mixture except for the total moles of propionyl produced (Moles Propionyl) which were calculated as described above.

EXAMPLES 22–30

The procedure described in Example 21 was repeated for Examples 22–30 with the exception that (i) 40 mmol of tetrabutylphosphonium iodide was used in Example 22 and (ii) in Examples 23–30 the tetrabutylphosphonium iodide was replaced with the secondary catalyst component (mmol) listed below:

| Example 23 | Sodium Iodide | (100) |
|---|---|---|
| Example 24 | Lithium Iodide | (100) |
| Example 25 | Potassium Iodide | (100) |
| Example 26 | Tetrabutylammonium Iodide | (100) |
| Example 27 | Tetra-n-octylphosphonium Iodide | (40) |
| Example 28 | Cesium Iodide | (100) |
| Example 29 | Triphenylphosphine | (100) |
| Example 30 | Triphenylphosphine Oxide | (100) |

The analytical results obtained from Examples 22–30 and the total moles of propionyl produced in each example are shown in Table II.

EXAMPLE 31

The procedure described in Example 21 was repeated except that 95.3 g of 47% aqueous hydrogen iodide (0.35 moles as HI) was used in place of ethyl iodide. The analytical results are shown in Table II.

TABLE II

| Example | Ethyl Propionate | Acetic Acid | Propionic Acid | Moles Propionyl |
|---|---|---|---|---|
| 21 | 1.1 | 33.4 | 38.7 | 2.85 |
| 22 | 0.8 | 38.3 | 22.9 | 1.47 |
| 23 | 1.2 | 38.6 | 35.8 | 2.29 |
| 24 | 1.0 | 44.9 | 14.0 | 0.79 |
| 25 | 0.6 | 46.0 | 14.6 | 0.79 |
| 26 | 0 | 36.6 | 27.3 | 1.80 |
| 27 | 0 | 39.0 | 13.6 | 0.89 |
| 28 | 1.4 | 39.0 | 36.i | 2.29 |
| 29 | 0 | 39.6 | 28.2 | 1.71 |
| 30 | 1.4 | 45.2 | 21.4 | 1.19 |
| 31 | 0 | 46.6 | 15.2 | 0.86 |

EXAMPLE 32

To allow the measurement of reaction rates, a 2 L autoclave constructed of a corrosion-resistant alloy was fitted with a high pressure condenser and a dip tube for removing samples during the course of the reaction. To the autoclave was added 5.81 g (0.022 moles) of Mo(CO)6, 19.3 g (0.050 moles) of tetrabutylphosphonium iodide, 109.2 g (0.700 moles) of ethyl iodide and 555 g (7.5 moles) of propionic acid. The condenser temperature is set at 5–10° C. using a cooled ethylene glycol/water mixture. The autoclave then was pressure tested with nitrogen at 68.9 bar (1000 psi) and a gas purge of 2 moles/hour of gas was established through the high pressure condenser. During the reaction this gas purge permits control of the gas composition over the reaction mixture and is necessary for kinetic measurements.

The nitrogen was vented off, the autoclave was pressurized to 24.1 bar (350 psi) with 5% hydrogen in carbon monoxide, and then heated to 180° C. The 2 moles/hour of gas purge is maintained throughout heating and the subsequent reaction. The pressure is raised to 55.1 bar (800 psi) using a gas mixture consisting of 7%$H_2$, 48% CO, and 45% ethylene while using the 2 mole/hour purge to maintain the gas mixture. Liquid samples are removed every 20 minutes for 5 hours and analyzed for ethyl iodide, ethyl propionate, propionic anhydride, and propionic acid. Gas samples also are removed hourly and analyzed by GC to insure that the gas mixture is consistent. The molar quantities of propionic anhydride ($n_{pan}$) formed were determined from the GC data using the following equation:

$$n_{pan} = \frac{X_{pan}}{130} \cdot \frac{n_{pa}^o + n_{ei}^o}{[(X_{ei}/156) + (X_{pa}/74) + (X_{pan}/130) + (X_{ep}/102)]}$$

wherein $n_i$=moles of the component $X_i$=weight fraction of the component (obtained from GC analysis)

$n_{pa}^o$=moles of propionyl initially present=propionic acid added at start $n_{ei}^o$=ethyl iodide initially added Wt=Weight of reaction mixture and ep=ethyl propionate; pa=propionic acid; pan=propionic anhydride; and ei=ethyl iodide.

The molar quantities were plotted against time and the reaction displayed an essentially linear behavior over the first 100 minutes of the reaction. Therefore, the rate of the reaction (expressed as moles of propionic anhydride formed/ kg. of initial reaction solution/hour) was readily determined by using a best fit slope of this plot over the course of the first 100 minutes of the reaction. This is consistent with the general practice in the art since conversions do not exceed 35% and are consistent with the method of initial rates. Using this method, the rate of propionic anhydride formation was determined to be 1.69 moles/kg-hour (236 g/kg-hr).

EXAMPLE 33

Example 32 was repeated except that the hydrogen was omitted from the feed gas. The rate of propionic anhydride formation decreased to 1.24 moles/kg-hr (174 g/kg-hr) thus demonstrating the beneficial effect of including hydrogen in the feed.

EXAMPLE 34

To demonstrate that nickel acts as an inhibitor of the hydroxycarbonylation process of this invention, Example 32 was repeated except that 2.49 g (0.010 moles) of nickel acetate tetrahydrate was also added. The rate of the reaction was 0.88 moles/kg-hr (123 g/kg-hr).

EXAMPLE 35

To demonstrate that iron acts as an inhibitor of the process, Example 32 was repeated except that 1.74 g (0.010 moles) of ferrous acetate also was added. The rate of the reaction was 0.43 moles/kg-hr (60 g/kg-hr).

EXAMPLE 36

Example 32 was repeated, except that the amount of ethyl iodide was reduced to 31.2 g (0.20 moles). The rate of propionic anhydride formation was 1.32 moles/kg-hr (185 g/kg-hr) thus demonstrating the process may be operated with substantially lower concentration of iodine.

The invention has been described in detail with particular reference to preferred embodiments thereof, but it will be understood that variations and modifications can be effected within the spirit and scope of the invention.

We claim:

1. Process for the preparation of an aliphatic carbonyl compound selected from aliphatic carboxylic acids, alkyl esters of aliphatic carboxylic acids and anhydrides of aliphatic carboxylic acids which comprises contacting carbon monoxide with a mixture comprising an olefin and a catalyst system comprising (1) a primary component selected from at least one Group 6 metal and (2) a secondary component selected from at least one of:

(i) a halide selected from the compounds of chlorine, bromine or iodine;

(ii) an alkali metal compound;

(iii) a salt of a quaternary organic compound of a Group 15 element;

(iv) a trisubstituted organic compound of a Group 15 element; and (v) an oxide of a trisubstituted phosphine compound;

under conditions of carbonylation temperature and at a pressure of about 8 to about 104 bar absolute, wherein the Group 6 metal is present in a concentration of 0.0001 to 1M and the process is carried out in the substantial absence of (1) metals of Groups 8, 9 and 10 and (2) formic acid and formate esters.

2. Process according to claim 1 wherein the olefin contains 2 to 20 carbon atoms and the temperature is about 75 to 350° C.

3. Process according to claim 2 wherein the catalyst system comprises (A) at least one Group 6 metal, (B) at least 1 iodine compound and (C) at least 1 component selected from a salt of an alkali metal, a salt of a quaternary phosphonium compound, a trisubstituted phosphine or a trisubstituted phosphine oxide, and the olefin contains 2 to 8 carbon atoms.

4. Process for the preparation of an aliphatic carbonyl compound selected from aliphatic carboxylic acids, alkyl esters of aliphatic carboxylic acids and anhydrides of aliphatic carboxylic acids which comprises contacting carbon monoxide with a mixture comprising an olefin, an organic solvent and a catalyst system comprising (A) at least one Group 6 metal, (B) at least 1 iodine compound and (C) at least 1 component selected from a salt of an alkali metal, a salt of a quaternary phosphonium compound, a trisubstituted phosphine or a trisubstituted phosphine oxide, and the olefin contains 2 to 8 carbon atoms, wherein the Group 6 metal is present in a concentration of 0.0001 to 1M and the process is carried out at a pressure of about 18 to 104 bar absolute, at a temperature of about 150 to 250° C., and in the substantial absence of (1) any metal of Groups 8, 9 and 10 and (2) formic acid and formate esters.

5. Process according to claim 4 wherein the solvent is an aliphatic carboxylic acid and the catalyst system comprises (A) molybdenum, (B) hydrogen iodide, an alkyl iodide or a mixture thereof, and (C) an iodide salt of an alkali metal, an iodide salt of a quaternary phosphonium compound, a trisubstituted phosphine or a trisubstituted phosphine oxide, and the olefin contains 2 to 4 carbon atoms.

6. Process for the preparation of propionic acid which comprises contacting carbon monoxide with a mixture comprising ethylene and a catalyst system comprising (A) molybdenum in a concentration of 0.0001 to 1M, (B) hydrogen iodide, an alkyl iodide or a mixture thereof, and (C) at least one component selected from an iodide salt of an alkali metal, an iodide salt of a quaternary phosphonium compound, a trisubstituted phosphine or a trisubstituted phosphine oxide, and water at a pressure of about 18 to 104 bar absolute, at a temperature of about 150 to 250° C., and in the substantial absence of (1) any metal of Groups 8, 9 and 10 and (2) formic acid and formate esters.

* * * * *